US011220904B2

(12) United States Patent
Brown et al.

(10) Patent No.: US 11,220,904 B2
(45) Date of Patent: *Jan. 11, 2022

(54) FLUID FLOW CONDITION SENSING PROBE

(71) Applicant: Halliburton Energy Services, Inc., Houston, TX (US)

(72) Inventors: Donn J. Brown, Broken Arrow, OK (US); Ketankumar Kantilal Sheth, Tulsa, OK (US); Robert C. de Long, Sand Springs, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 62 days.

This patent is subject to a terminal disclaimer.

(21) Appl. No.: 16/825,965

(22) Filed: Mar. 20, 2020

(65) Prior Publication Data

US 2021/0293140 A1 Sep. 23, 2021

(51) Int. Cl.
*E21B 49/08* (2006.01)
*E21B 43/12* (2006.01)
*E21B 17/10* (2006.01)
*E21B 47/12* (2012.01)
*E21B 47/06* (2012.01)
*E21B 47/07* (2012.01)
*G01N 33/28* (2006.01)
*E21B 47/10* (2012.01)

(52) U.S. Cl.
CPC .......... *E21B 49/08* (2013.01); *E21B 17/1078* (2013.01); *E21B 43/128* (2013.01); *E21B 47/06* (2013.01); *E21B 47/07* (2020.05); *E21B 47/10* (2013.01); *E21B 47/12* (2013.01); *G01N 33/2823* (2013.01); *E21B 49/0875* (2020.05)

(58) Field of Classification Search
CPC ...... E21B 49/08; E21B 47/07; E21B 17/1078; E21B 47/06; E21B 43/121; E21B 43/128; E21B 47/10; E21B 47/12; E21B 49/0875; F04D 13/086; F04D 13/08
See application file for complete search history.

(56) References Cited

U.S. PATENT DOCUMENTS

| 7,607,896 B2 | 10/2009 | Leuthen et al. |
| 7,798,215 B2 | 9/2010 | Leuthen et al. |
| 10,472,946 B2 | 11/2019 | Chokshi et al. |

(Continued)

FOREIGN PATENT DOCUMENTS

WO WO-2018007026 A1 * 1/2018 ............. E21B 47/01

OTHER PUBLICATIONS

Foreign Communication from Related Application—International Search Report and Written Opinion of the International Searching Authority, International Application No. PCT/US2020/024885, dated Dec. 10, 2020, 13 pages.

(Continued)

*Primary Examiner* — Caroline N Butcher
(74) *Attorney, Agent, or Firm* — Conley Rose, P.C.; Rodney B. Carroll (57) ABSTRACT

An electric submersible pump (ESP) assembly. The ESP assembly comprises an electric motor, a centrifugal pump mechanically coupled to the electric motor, and a probe mechanically coupled to the electric motor and extending upstream of the electric motor, comprising a plurality of sensor bundles distributed axially along the probe wherein each sensor bundle comprises at least one sensor.

20 Claims, 6 Drawing Sheets

(56) References Cited

U.S. PATENT DOCUMENTS

| | | |
|---|---|---|
| 2002/0074127 A1 | 6/2002 | Birckhead et al. |
| 2003/0015320 A1 | 1/2003 | Crossley |
| 2003/0173072 A1 | 9/2003 | Vinegar et al. |
| 2004/0238167 A1 | 12/2004 | Pinto et al. |
| 2009/0283258 A1* | 11/2009 | Poitzsch ................. E21B 47/01 166/250.1 |
| 2013/0175030 A1* | 7/2013 | Ige ......................... G05B 15/02 166/250.15 |
| 2018/0347346 A1 | 12/2018 | Gouda et al. |

OTHER PUBLICATIONS

Office Action (26 pages), dated Apr. 21, 2021, U.S. Appl. No. 16/825,969, filed Mar. 20, 2020.

Filing Receipt, Specification and Drawings for U.S. Appl. No. 16/825,969, filed Mar. 20, 2020, entitled "Fluid Flow Condition Sensing Probe," 54 pages.

Foreign Communication from Related Application—International Search Report and Written Opinion of the International Searching Authority, International Application No. PCT/US2020/024889, dated Dec. 3, 2020, 13 pages.

\* cited by examiner

FLUID FLOW CONDITION SENSING PROBE

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Wells may be drilled to access hydrocarbons pooled in subterranean formations. Sometimes the hydrocarbons may flow naturally to the surface, at least after initially bringing a well on-line after completion. As reservoir pressure drops, however, many wells apply some kind of artificial lift mechanism to assist production of hydrocarbons to the surface. Artificial lift methods comprise electric submersible pumps (ESPs), rod lift, plunger lift, gas lift, charge pumps, and other lift methods. Fluid flow conditions in the wellbore may change significantly over the production lifecycle of a well. Pressure conditions may vary, a viscosity of production fluid can vary. Water can break into the hydrocarbon fluid flow, initially reducing viscosity and then increasing the fluid viscosity as emulsification of the water in oil occurs. Steam may break into the fluid flow and temperatures may increase significantly. These changing conditions can adversely affect the reliability and service life of artificial lift equipment.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

As used herein, orientation terms "upstream," "downstream," "up," and "down" are defined relative to the direction of flow of well fluid in the well casing. "Upstream" is directed counter to the direction of flow of well fluid, towards the source of well fluid (e.g., towards perforations in well casing through which hydrocarbons flow out of a subterranean formation and into the casing). "Downstream" is directed in the direction of flow of well fluid, away from the source of well fluid. "Down" is directed counter to the direction of flow of well fluid, towards the source of well fluid. "Up" is directed in the direction of flow of well fluid, away from the source of well fluid.

Conventional artificial lift systems adapt to changing production parameters, if at all, in a reactive way. First a production parameter changes, then controllers adapt operation of the artificial lift system. In an example, sand may break from the subterranean formation and plug the pump suddenly, and the drive shaft of an electric submersible pump (ESP) assembly may break before the controller at the surface can adapt operation of the ESP assembly. The present disclosure teaches adding a sensor probe to an upstream end of the ESP assembly. The sensor probe comprises one or more bundles of sensors that can sense wellbore conditions and fluid conditions upstream of the remainder of the ESP assembly and communicate these parameter values to a controller at the surface. These sensors can provide wellbore fluid condition indications to the controller before these fluid conditions arrive at the pump, and therefore the controller can adapt the operation of the ESP assembly proactively, before the subject conditions are experienced by the ESP assembly. The sensors may be spatially distributed along the probe, whereby a fluid flow velocity associated with a fluid parameter change from an otherwise steady state of the fluid parameter value may be determined by the controller.

In an embodiment, the sensor probe comprises at least one centralizer. One or more centralizers coupled to the sensor probe may keep the sensors about in the middle of the wellbore and/or close to the centerline of the wellbore, and this positioning of the sensors may promote the sensors obtaining more accurate data on the fluid conditions. By positioning the sensors away from the casing and close to the centerline of the wellbore, the centralizers may also protect the sensors from damaging impacts with the casing or with other items in the wellbore.

In the example of sand breaking into a wellbore described above, the sensor probe can provide sensed parameter values correlating with breaking sand to the controller, and the controller can adapt the operation of the ESP assembly (e.g., turn the motor off) and avoid severe damage to the ESP assembly. There are a wide variety of changed wellbore conditions and fluid flow conditions that the sensor probe can detect and report to the controller before the conditions reach the ESP assembly.

Figure 1A:
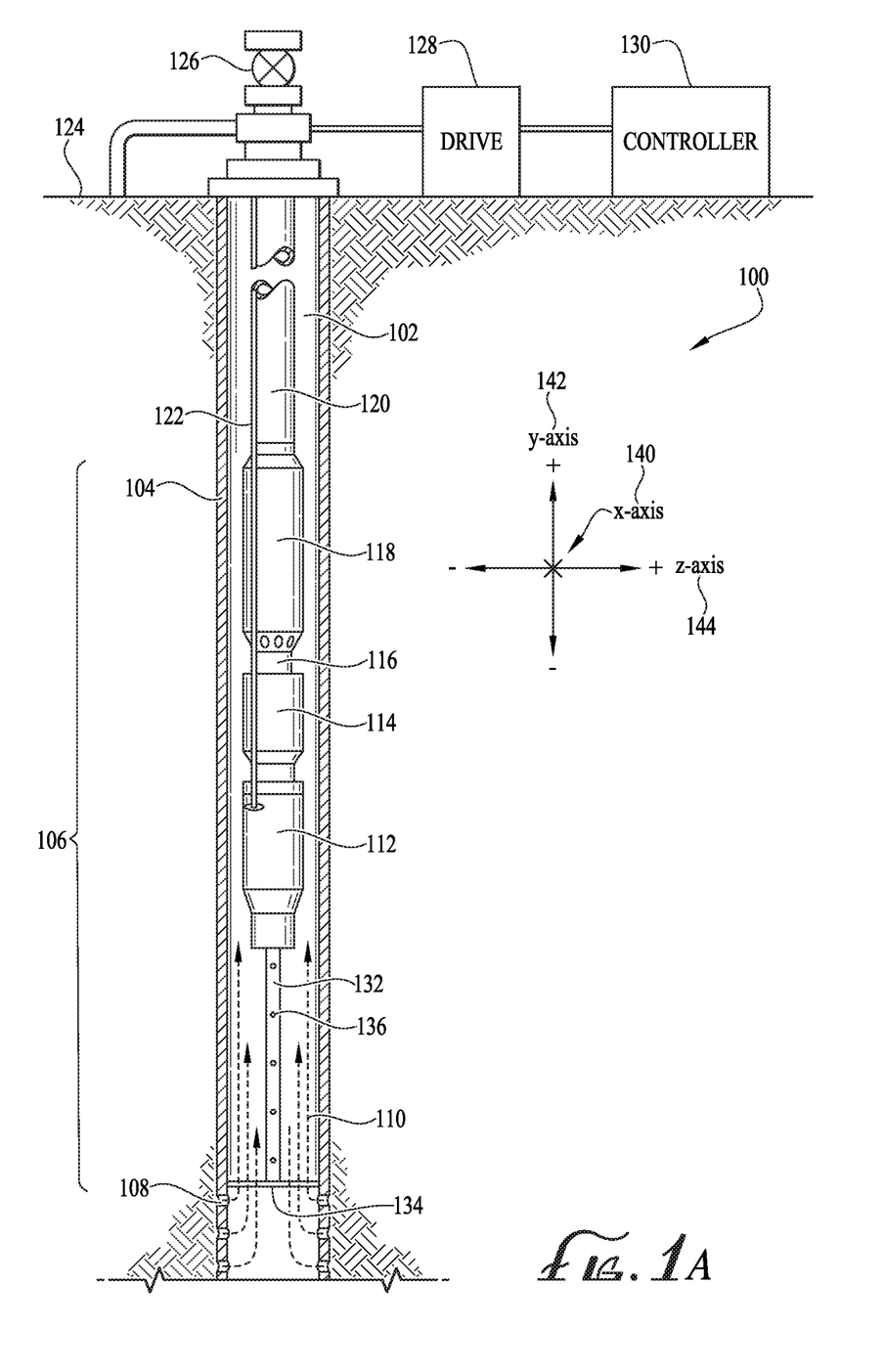
FIG. 1A is an illustration of a wellbore and an exemplary well completion according to an embodiment of the disclosure.

Turning now to FIG. 1A, a production system 100 is described. In an embodiment, the system 100 comprises a wellbore 102, a casing 104, and an electric submersible pump (ESP) assembly 106. The casing 104 may comprise a plurality of perforations 108 that allow fluid 110 to leave an adjacent subterranean formation, flow through the perforations 108, into the wellbore 102, and flow downstream to the ESP assembly 106. The ESP assembly 106 comprises an electric motor 112, a seal unit 114, a pump intake 116, and a centrifugal pump 118. An outlet of the pump 118 is coupled to production tubing 120. An electric power cable 122 electrically connects the ESP assembly 106 (e.g., the electric motor 112) to an electric drive 128 that is controlled by a controller 130. When the ESP assembly 106 is operated (when the electric drive 128 powers the electric motor 112, and the electric motor 112 turns the centrifugal pump 118), the fluid 110 may enter the pump intake 116 and be pumped by the ESP assembly 106 to a wellhead 126 located at the surface 124. In an embodiment, the electric drive 128 may be a variable speed drive The ESP assembly 106 further comprises a sensor probe 132. One or more centralizers 134 are coupled to the sensor probe 132 and hold the axis of the sensor probe 132 about coincident with a longitudinal axis of the wellbore 102. The centralizers 134 are configured to avoid interfering with the flow of the fluid 110 downstream to the pump intake 116. One or more sensor bundles 136 are coupled to the sensor probe 132. The sensor bundles 136 may be removably coupled to the sensor probe 132. For example, the sensor bundles 136 may be configured to be easily removed from the sensor probe 132 when pulling the ESP assembly 106 out of the wellbore 102 for servicing and to be easily attached (e.g., a replacement set of new or refurbished sensor bundles 136) to the sensor probe 132 when running the serviced ESP assembly 106 back into the wellbore 102.

The sensor bundles 136 sense proximate conditions of the wellbore 102 and/or of the fluid 110 and communicate sensed parameter values to the controller 130. The sensor bundles 136 may communicate by wired communication (e.g., via the electric power cable 122, for example using power line communication (PLC) techniques), via wired communication, or via acoustic or hydraulic communication to the surface 124 and/or to the controller 130. The sensor bundles 136 may comprise communication components or modules that promote communicating the sensor data to the controller 130, for example using wired communication, wireless communication, acoustic communication, and/or hydraulic communication.

FIG. 1A provides a directional reference comprising three coordinate axes—an X-axis 140 where positive displacements along the X-axis 140 are directed into the sheet and negative displacements along the X-axis 140 are directed out of the sheet; a Y-axis 92 where positive displacements along the Y-axis 142 are directed upwards on the sheet and negative displacements along the Y-axis 142 are directed downwards on the sheet; and a Z-axis 144 where positive displacements along the Z-axis 144 are directed rightwards on the sheet and negative displacements along the Z-axis 144 are directed leftwards on the sheet. The Y-axis 142 is about parallel to a central axis of a vertical portion of the wellbore 102.

The sensor probe 132 may be any desirable length. In an embodiment, the sensor probe 132 may be at least about 10 feet long, less than about 50 feet long, less than about 100 feet long, less than about 150 feet long, less than about 200 feet long, less than about 300 feet long, less than about 400 feet long, less than about 500 feet long, less than about 750 feet long, less than about 900 feet long, less than about 1000 feet long, or some other length. In an embodiment, the sensor probe 132 may be at least about 10 feet long and less than about 1000 feet long. In an embodiment, the sensor probe 132 may be at least 10 feet long and less than about 300 feet long.

In an embodiment, a length of the sensor probe 132 may be determined by a designer based in part on a projection of a distance fluid flows downstream in the wellbore 102 per unit of time during production, for example, a maximum distance flowed per unit of time may be used. The length of the sensor probe 132 may be determined further based on a latency of adaptation of the operation of the ESP assembly 106 by the controller 130 (e.g., how fast can the controller 130 command the ESP assembly 106 to a different operating configuration in response to changed inputs from sensor bundles 136). For example, if the controller 130 can adapt operation of the ESP assembly 106 to a changed wellbore condition and/or fluid flow condition in 5 seconds and the fluid 110 is projected to flow at a maximum speed of 10 feet per second in the wellbore 102 upstream of the electric motor 112, the sensor probe 132 may desirably be at least 50 feet long and less than 75 feet long. If, instead, the fluid 110 is projected to flow at a maximum speed of 20 feet per second in the wellbore 102 upstream of the electric motor 112, the sensor probe 132 may desirably be at least 100 feet long and less than 150 feet long. If the controller 130 can adapt operation of the ESP assembly 106 to a changed wellbore condition and/or fluid flow condition in 2 seconds, the sensor probe 132 may be at least 20 feet long (in first example of fluid flowing at 10 feet per second) and less than 30 feet long; or the sensor probe 132 may be at least 40 feet long (in the second example of fluid flowing at 20 feet per second) and less than 60 feet long.

Each sensor bundle 136 may comprise a plurality of sensors, each sensor associated with sensing and transmitting data on different fluid flow or wellbore condition parameters. One of the sensors may sense and report temperature. Another sensor may sense and report fluid flow rate. Another sensor may sense and report fluid viscosity. Another sensor may sense and report fluid density. Another sensor may sense and report audio signals. Audio signals, for example, may be analyzed to infer the presence of particulate matter such as sand breaking into the wellbore 102. Another sensor may sense and report pressure. Another sensor may sense and report scale build up. Another sensor may sense and report a vibration. Another sensor may sense and report an acceleration. The sensor bundle 136 may comprise at least one sensor selected from the group consisting of a temperature sensor, a flow rate sensor, a pressure sensor, a density sensor, a viscosity sensor, an acoustic sensor, a vibration sensor, and an acceleration sensor.

In an embodiment, one or more of the sensors may be a microelectromechanical system (MEMS) sensor. In some contexts, MEMS sensors may also be referred to as microsystems technology sensors or micromachined sensors. MEMS devices generally, and MEMS sensors in particular, may be fabricated using microfabrication techniques such as those used for manufacturing semiconductors. MEMS devices may be built on a semiconductor substrate and built up progressively by a sequence of chemical deposition operations followed by corresponding etching operations to create the desired microcircuits and the desired micromechanical structures on the semiconductor substrate. MEMS devices may integrate mechanical structures, analog electronics, and signal conditioning electronics on a single chip. A plurality of MEMS devices may be built up on the same semiconductor wafer and then cut into a plurality of dice that each contains a MEMS device. These separated dice may then be mounted on separate packages for distribution and installation in systems, for example in the sensor bundles 136 of this disclosure. It is an advantage of MEMS devices that they benefit from the same low per unit production costs and high consistency of performance exhibited by semiconductor devices.

In some cases, the MEMS sensors may be built on a silicon wafer. In other cases, however, the MEMS sensors may be built on a wafer having a different material that exhibits improved high temperature performance relative to silicon or improved performance in high pressure conditions relative to silicon. The MEMS sensors may be built on a wafer having a different material that exhibits greater resistance to corrosives present in a wellbore than does silicon. In an embodiment, the MEMS sensors herein may be build on a silicon carbide (SiC) substrate, or another material that exhibits like resistance to high temperature and corrosion. The MEMS sensors may be referred to as transducers in that they convert energy in one form to another form, for example from mechanical energy to electrical energy.

Some sensors in the sensor bundles 136, however, may not be MEMS sensors. Some sensors may be fiber optic sensors, for example temperature sensors may be fiber optic sensors. For example pressure sensors may be fiber optic sensors. Some fluid flow condition parameters may be derived from other physical parameters.

Figure 1B:
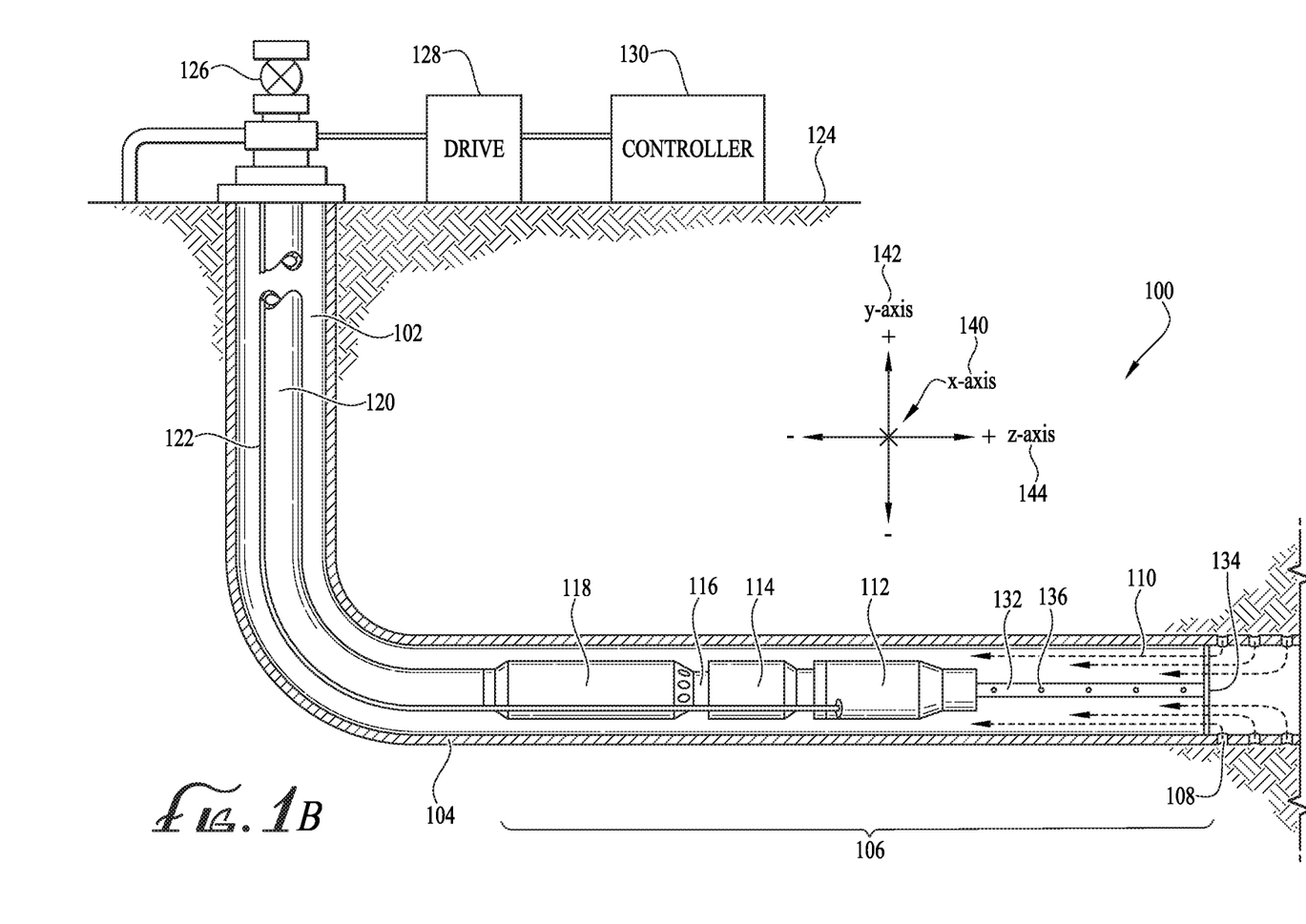
FIG. 1B is an illustration of a wellbore and another exemplary well completion according to an embodiment of the disclosure.

Turning now to FIG. 1B, the production system 100 is shown where the completion of the well and/or ESP assembly 106 is in a deviated and/or horizontal portion of the wellbore 102. The components of the system 100 in FIG. 1B are the same as those illustrated in FIG. 1A, the difference being they are illustrated in the context of a wellbore 102 having a deviated and/or horizontal portion.

Figure 2:
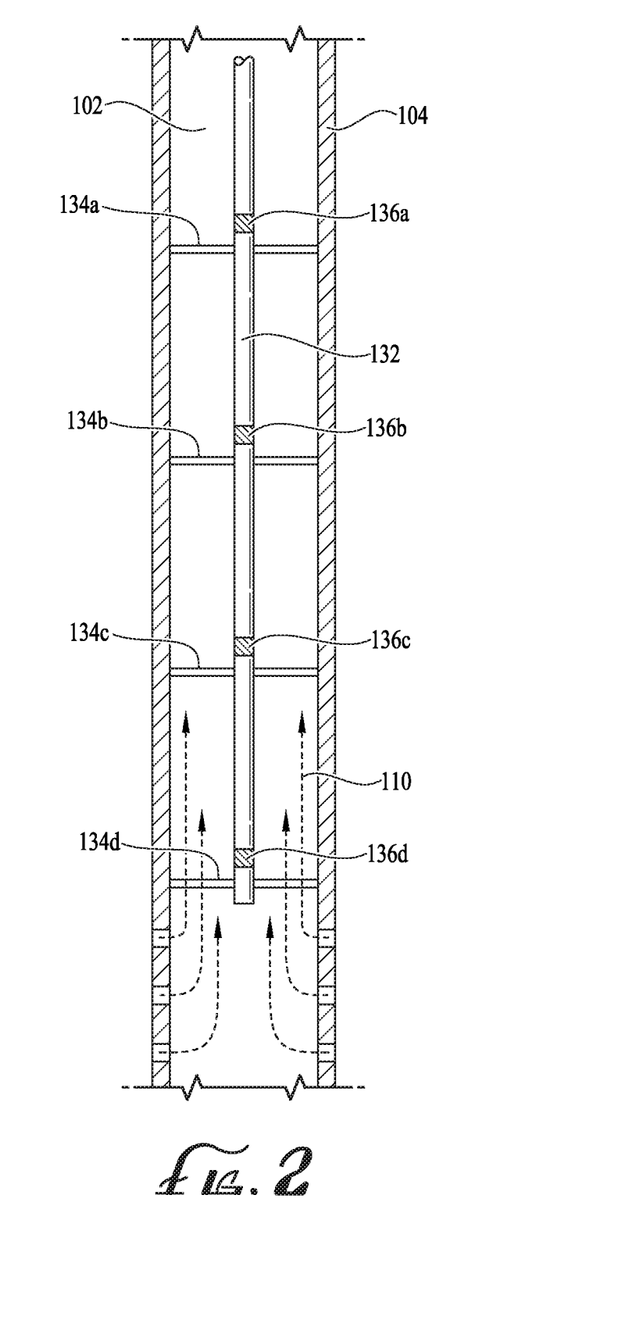
FIG. 2 is an illustration of a sensor probe according an embodiment of the disclosure.

Turning now to FIG. 2, further details of the sensor probe 132 are described. In an embodiment, the sensor probe 132 comprises a plurality of centralizers 134, for example a first centralizer 134a, a second centralizer 134b, a third centralizer 134c, and a fourth centralizer 134d. In an embodiment, the sensor probe 132 comprises a plurality of sensor bundles 136, for example a first sensor bundle 136a, a second sensor bundle 136b, a third sensor bundle 136c, and a fourth sensor bundle 136d. While four sensor bundles 136 are illustrated in FIG. 2, it is understood that the sensor probe 132 may comprise two sensor bundles 136, three sensor bundles 136, five sensor bundles 136, six sensor bundles 136, seven sensor bundles 136, eight sensor bundles 136, nine sensor bundles 136, ten sensor bundles 136, fourteen sensor bundles 136, fifteen sensor bundles 136, sixteen sensor bundles 136, eighteen sensor bundles 136, twenty sensor bundles 136, or some other number of sensor bundles 136.

The structure of the sensor probe 132 may be provided by pipe joints coupled to each other. In an embodiment, the upstream end of the pipe joint furthest downhole may be capped. The capping of the pipe joint may prevent reservoir fluid 110 and/or gas from entering the interior of the pipe joints that form the structure of the sensor probe 132 in this embodiment. The structure of the sensor probe 132 can be provided by solid metal rods with ends coupled to each other to string a plurality of rods end-to-end. In some contexts, the sensor probe 132 may be referred to as a stinger.

The sensor bundles 136 may be axially displaced from each other along the sensor probe 132. The sensor bundles 136 may be spaced about an equal distance away from each other. The sensor bundles 136 may be separated by about 2 feet, about 10 feet, about 20 feet, about 30 feet, about 40 feet, about 60 feet, about 80 feet, about 100 feet, about 150 feet, about 180 feet, or some other distance from each other. Alternatively, in an embodiment, the sensor bundles 136 may be spaced at different distances from each other. In an embodiment, the first and the second sensor bundles 136a, 136b may be spaced close to each other and the third and the fourth sensor bundles 136c, 136d may be spaced close to each other. In this disposition, the first and second sensor bundles 136a, 136b may measure parameter values of the reservoir fluid 110 at about the same place in the wellbore 102, thereby providing redundancy of measurement at that first location in case of failure of a single one of the sensor bundles 136a, 136b. The third and fourth sensor bundles 136c, 136d may measure parameter values of the reservoir fluid 110 in about the same place in the wellbore 102 (upstream of the sensor bundles 136a, 136b), thereby providing redundancy of measurement at that second location in case of failure of a single one of the sensor bundles 136c, 136d.

Each centralizer 134 may be located proximate to a corresponding sensor bundle 136. The sensor probe 132 may comprise any number of centralizers 134 and any number of sensor bundles 136. In an embodiment, more than a single centralizer 134 is proximate to each sensor bundle 136. For example, a centralizer 134 may be located proximate to a sensor bundle 136 on the upstream side of the sensor bundle 136 and another centralizer 134 may be located proximate to the same sensor bundle 136 on the downstream side of the sensor bundle 136. In an embodiment, additional centralizers 134 may be located about mid-way between sensor bundles 136 or at other intermediate locations in addition to being located proximate to the sensor bundles 136. In an embodiment, the sensor probe 132 comprises a plurality of centralizers 134, wherein each sensor bundle 136 is associated with at least one centralizer 134 located proximate to the sensor bundle 136. In an embodiment, each sensor bundle 136 is associated with a centralizer 134 located upstream and proximate to the sensor bundle 136 and with a centralizer located downstream and proximate to the sensor bundle 136. As used herein, a centralizer 134 said to be located proximate to a sensor bundle 126 may be located within about 2 feet of the sensor bundle 126, located within about 1 foot of the sensor bundle 126, located within about 9 inches of the sensor bundle 126, located within about 6 inches of the sensor bundle 126, located within about 4 inches of the sensor bundle 126, located within about 3 inches of the sensor bundle 126, located within about 2 inches of the sensor bundle 126, or located within about 1 inch of the sensor bundle.

The centralizers 134 keep the sensor bundles 136 in the center of the wellbore 102. The fluid flow parameter values sensed and communicated by the sensor bundles 136 to the controller 130 may be more accurate being measured by the sensor bundles 136 located in the middle of the wellbore 102, because the flow of the reservoir fluid 110 in the middle of the wellbore 102 may be more representative of the flow of the reservoir fluid 110 in the wellbore 102 than would a measurement taken close to the casing 104. Additionally, keeping the sensor bundles 136 centralized in the wellbore 102 while running the ESP assembly 106 and the sensor probe 132 into the wellbore 102 can protect the sensor bundles 136 from potentially damaging impacts with the casing 104 and/or structures located close to the casing walls, for example casing hangers, multilateral junctions, and other devices.

Each sensor bundle 136 may comprise a plurality of sensors, for example two or more of a temperature sensor, a pressure sensor, a flow-rate sensor, a density sensor, a viscosity sensor, and/or an acoustic sensor. The several sensors in a sensor bundle 136 may individually communicate back to the controller 130. Alternatively, the several sensors in a sensor bundle 136 may individually communicate back to a hub located at the electric motor 112, the seal unit 114, or the pump 118, and this hub may communicate the received sensor data to the controller 130. Alternatively, each sensor bundle 136 may comprise a hub that aggregates sensor data from the sensor data collected by the individual sensors of the sensor bundle 136 and communicate the aggregated sensor data to the controller 130. Alternatively, each sensor bundle 136 may comprise a hub that aggregates sensor data from the sensor data collected by the individual sensors of the sensor bundle 136 and communicate the aggregated sensor data back to another hub located at the electric motor 112, the seal unit 114, or the pump, and this other hub may communicate the aggregated sensor data collected from all the sensor bundles 136 to the controller 130. In an embodiment, the ESP assembly 106 comprises at least one communication hub that is configured to receive sensor data from a plurality of sensors and to send the sensor data to the controller 130. In an embodiment, the ESP assembly 106 comprises at least one communication hub that is configured to receive sensor data from a plurality of sensor bundles 136 and to send the sensor data to the controller 130.

The sensor bundles 136 may be replaced when the ESP assembly 106 and the sensor probe 132 is pulled out of the wellbore 102, for example to service, to refurbish, and/or to replace the ESP assembly 106. By replacing the sensor bundles 136, the likelihood that a sensor bundle 136 will fail downhole and degrade the ability of the controller to proactively operate the ESP assembly 106 in varying fluid flow conditions can be reduced.

With reference to FIG. 1A, FIG. 1B, and FIG. 2, the controller 130 may receive sensor data from the sensor probe 132 that can be analyzed to infer fluid flow and wellbore conditions at the ESP assembly 106 and/or at the pump intake 116. When the fluid 110 is in a steady state, the sensor data may remain largely unchanged over a significant amount of time, for example over days, over weeks, even over months. But when significant changes in the fluid 110 do occur, they can occur suddenly and significantly impact the operation of the ESP assembly 106. Providing multiple sensor bundles 136 coupled to the sensor probe 132 promotes determining a rate of change of the fluid flow parameters and estimating a fluid flow distance per unit time (e.g., a fluid flow velocity). By providing a plurality of sensor bundles 136, one or more sensor bundle 136 may fail without preventing the controller 130 from accurately determining fluid flow parameters.

It is understood that the sensor probe 132 can advantageously be used with other artificial lift methods to adapt the control of those other artificial lift mechanisms by the controller 130 based on sensor data related to changing fluid flow and/or wellbore conditions. For example, rod lift, plunger lift, gas lift, and gas lift mechanisms can be stopped to prevent sand inflow at the lift intake.

In some production environments hydrocarbons are disposed in oil sands or tar sands and do not readily flow in their ordinary state. In steam assisted gravity drainage (SAGD), a horizontal wellbore may be drilled parallel to and above another horizontal wellbore. Steam may be pumped into the upper horizontal wellbore to heat the proximate tar sand formation. The heavy hydrocarbons show reduced viscosity when heated, flow by influence of gravity into the lower horizontal wellbore, and are lifted to the surface by the ESP assembly 106. Over time, however, the high pressure, high temperature steam may break into the lower wellbore and propagate in the lower wellbore to the ESP assembly 106. This high temperature steam and associated water can severely impact operation of the ESP assembly 106. First, the high temperature can cause rapid damage to the electric motor 112 due to temperature effects in the motor (e.g., insulation breakdown and premature aging of the motor coils). Second, the presence of water in the fluid 110 can significantly change the viscosity of the fluid 110 and impact performance of the ESP assembly 106. By sensing both the high temperature and the viscosity change by the sensor bundles 136 and sending this sensor data to the controller 130, the controller 130 is able to adapt proactively the operation of the ESP assembly 106 accordingly. In an embodiment, the controller 130 may stop the electric motor 112 by commanding the drive to stop providing electric current to the electric motor 112. In the case that steam is breaking into the production wellbore 102, it may be prudent to interrupt continued injection of steam, to pull the ESP assembly 106 from the wellbore 102, and to close in the wellbore 102 at the wellhead 126. Production via this wellbore 102 may be terminated. Alternatively, a different completion assembly may be substituted for the previous ESP assembly 106 or a different production stimulation technique may be applied.

Sometimes a subterranean formation that is producing hydrocarbons can transition to producing sand. This may be referred to as sand breaking into the wellbore 102. Sand flowing into the pump intake 116 can cause the centrifugal pump 118 to be clogged by sand and stop suddenly, potentially causing the drive shaft that couples the electric motor 112 to the centrifugal pump 118 to break. The sensor probe 132 may provide sensor indications to the controller 130 that the controller 130 can use to infer sand breaking into the wellbore 102 upstream of the pump intake 116 and to command the drive 128 to stop or slow the electric motor 112 before the sand clogs the centrifugal pump 118. For example, an acoustic sensor may capture an audio signature of sand striking the acoustic sensor. Under these circumstances, the ESP assembly 106 may be pulled from the wellbore 102 unharmed by avoiding driving the centrifugal pump 118 while it is clogged with sand. Such sand clogging can occur so rapidly that reactive response to the onset of breaking sand is of no use. The proactive sensing and adaptation of ESP assembly operation 106 as described herein can avoid such sand caused damage.

Figure 3:
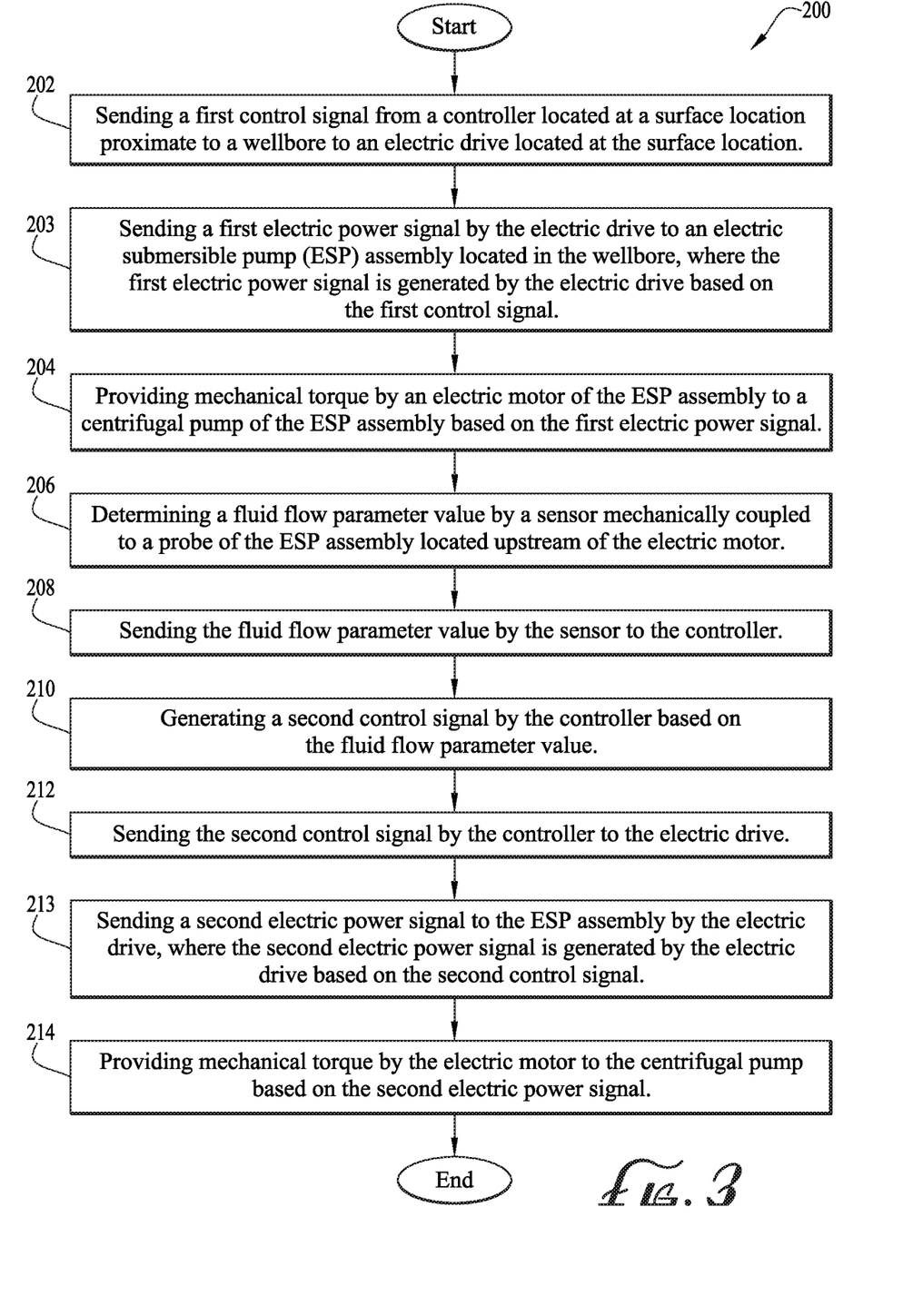
FIG. 3 is a flow chart of a method according to an embodiment of the disclosure.

Turning now to FIG. 3, a method 200 is described. In an embodiment, the method 200 comprises a method of artificially lifting fluid in a wellbore. At block 202, the method 200 comprises sending a first control signal from a controller located at a surface location proximate to a wellbore to an electric drive located at the surface location. The first control signal may be generated by the controller 130 based on a fluid flow parameter value received by the controller 130 at a first time from a sensor, for example by a sensor that is part of a sensor bundle 136. In an embodiment, the fluid flow parameter value is a fluid flow temperature, a fluid flow rate, a fluid flow pressure, a fluid flow density, or a fluid flow viscosity. The first control signal may be generated by the controller 130 based on a plurality of different fluid flow parameters, each different fluid flow parameter produced by a different sensor located in the same sensor bundle 136. Alternatively, the first control signal may be generated by the controller 130 based on a plurality of different fluid flow parameters, at least some of the different fluid flow parameters being received from sensors located in different sensor bundles 136 located at different displacements along the probe 132 (e.g., distributed axially along the probe). The first control signal may be generated by the controller 130 based on other sensor inputs, for example a vibration sensor input, an acceleration sensor input, and/or an acoustic sensor input.

At block 203, the method 200 comprises sending a first electric power signal by the electric drive to an electric submersible pump (ESP) assembly located in the wellbore, where the first electric power signal is generated by the electric drive based on the first control signal. The electric power signal may be a frequency of electric power output by the electric drive 128 to the electric motor 112, for example via the electric power cable 122. The electric power signal may be a voltage of electric power output by the electric drive 128 to the electric motor 112. The electric power signal may be both a frequency and a voltage of electric power output to the electric motor 112.

At block 204, the method 200 comprises providing mechanical torque by an electric motor of the ESP assembly to a centrifugal pump of the ESP assembly based on the first electric power signal. At block 206, the method 200 comprises determining a fluid flow parameter value by a sensor mechanically coupled to a probe of the ESP assembly located upstream of the electric motor. The fluid flow parameters may be a fluid pressure, a fluid temperature, a fluid viscosity, or a fluid density. The fluid flow parameters may be an acoustic and/or audio signal, for example a sound that betokens particulate matter (e.g., sand) entrained within the fluid 110. The different fluid flow parameter values may be provided by different sensors within the same sensor bundle 136 and/or sensors in multiple different sensor bundles 136.

At block 208, the method 200 comprises sending the fluid flow parameter value by the sensor to the controller. The processing of block 208 may comprise sending fluid flow parameter values from two or more difference sensor bundles to the controller. At block 210, the method 200 comprises generating a second control signal by the controller based on the fluid flow parameter value. The second control signal may be generated by the controller 130 based on a fluid flow parameter value received by the controller 130 at a second time from the sensor, where the second time is later than the first time. The second control signal may be generated by the controller 130 based on a plurality of different fluid flow parameters. The second control signal may be generated by the controller 130 based on other sensor inputs, for example a vibration sensor input, an acceleration sensor input, and/or an acoustic sensor input.

At block 212, the method 200 comprises sending the second control signal by the controller to the electric drive. At block 213, the method 200 comprises sending a second electric power signal to the ESP assembly by the electric drive, where the second electric power signal is generated by the electric drive based on the second control signal. In an embodiment, the first electric power signal is different from the second electric power signal in frequency. In an embodiment, the first electric power signal is different from the second electric power signal in voltage. In an embodiment, the first electric power signal is different from the second electric power signal in both frequency and in voltage. At block 214, the method 200 comprises providing mechanical torque by the electric motor to the centrifugal pump based on the second electric power signal.

Figure 4:
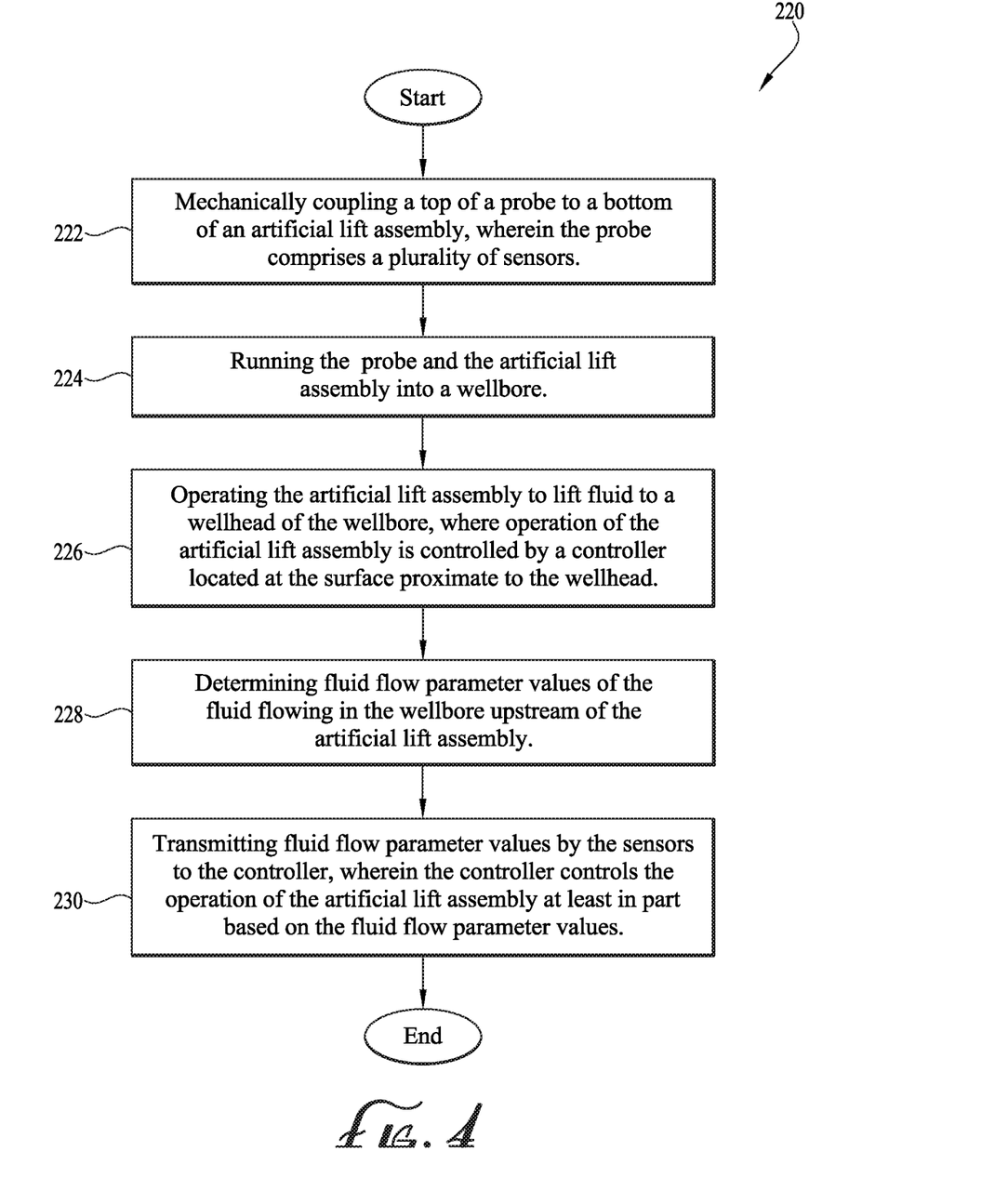
FIG. 4 is a flow chart of another method according to an embodiment of the disclosure.

Turning now to FIG. 4, a method 220 is described. In an embodiment, the method 220 comprises a method of artificially lifting fluid in a wellbore. At block 222, the method 220 comprises mechanically coupling a top of a probe to a bottom of an artificial lift assembly, wherein the probe comprises a plurality of sensors. In an embodiment, the method 220 further comprises mechanically coupling a plurality of sensor bundles 136 to the sensor probe 132, wherein each sensor bundle 136 comprises a plurality of sensors. The artificial lift assembly may be an electric submersible pump (ESP) assembly e.g., ESP assembly 106), a rod lift assembly, a plunger lift assembly, a gas lift assembly, or a charge pump assembly.

At block 224, the method 220 comprises running the probe and the artificial lift assembly into a wellbore. At block 226, the method 220 comprises operating the artificial lift assembly to lift fluid to a wellhead of the wellbore, where operation of the artificial lift assembly is controlled by a controller located at the surface proximate to the wellhead.

At block 228, the method 220 comprises determining fluid flow parameter values of the fluid flowing in the wellbore upstream of the artificial lift assembly. In an embodiment, the fluid flow parameter values comprise fluid flow rate and fluid pressure, fluid flow rate and fluid temperature, fluid flow rate and fluid density, fluid flow rate and fluid viscosity, fluid pressure and fluid temperature, fluid pressure and fluid viscosity, fluid pressure and fluid density, fluid temperature and fluid viscosity, fluid temperature and fluid density, or fluid density and fluid viscosity. In an embodiment, the processing of block 228 may comprise determining a first fluid flow parameter value by a first sensor mechanically coupled to a probe of the ESP assembly located upstream of the electric motor and determining a second fluid flow parameter value by a second sensor mechanically coupled to the probe of the ESP assembly, where the second sensor is located upstream of the first sensor (e.g., the first sensor and the second sensor may be located in different sensor bundles 136 spatially distributed axially along the probe 132).

At block 230 the method 220 comprises sending fluid flow parameter values by the sensors to the controller, wherein the controller controls the operation of the artificial lift assembly at least in part based on the fluid flow parameter values.

In an embodiment, the controller may infer fluid flow parameters, for example a flow rate or a velocity of the fluid 110, based on analyzing fluid flow parameter values that are different from a flow rate parameter value. For example, the controller 130 may receive a temperature fluid flow parameter value from the fourth sensor bundle 136*d* at a first time that is different from a temperature fluid flow parameter value received from the third sensor bundle 136*c*. At a second later time, the controller 130 may receive a temperature fluid flow parameter value from the fourth sensor bundle 136*d* that is equal to a temperature fluid flow parameter value received from the third sensor bundle 136*c*. The controller 130 may calculate that the fluid 110 has traveled the distance between the fourth sensor bundle 136*d* and the third sensor bundle 136*c* during the time that has passed from the first time to the second time. From this time interval and from the known axial distance that separates the fourth sensor bundle 136*d* and the third sensor bundle 136*c*, the controller 130 may calculate a fluid flow velocity, for example 5 feet per second or some other flow rate. The controller may alternatively calculate the fluid flow rate in volume flow per unit of time based on a known diameter of the casing 104 and based on the known axial distance that separates the fourth sensor bundle 136*d* and the third sensor bundle 136*c*.

Figure 5:
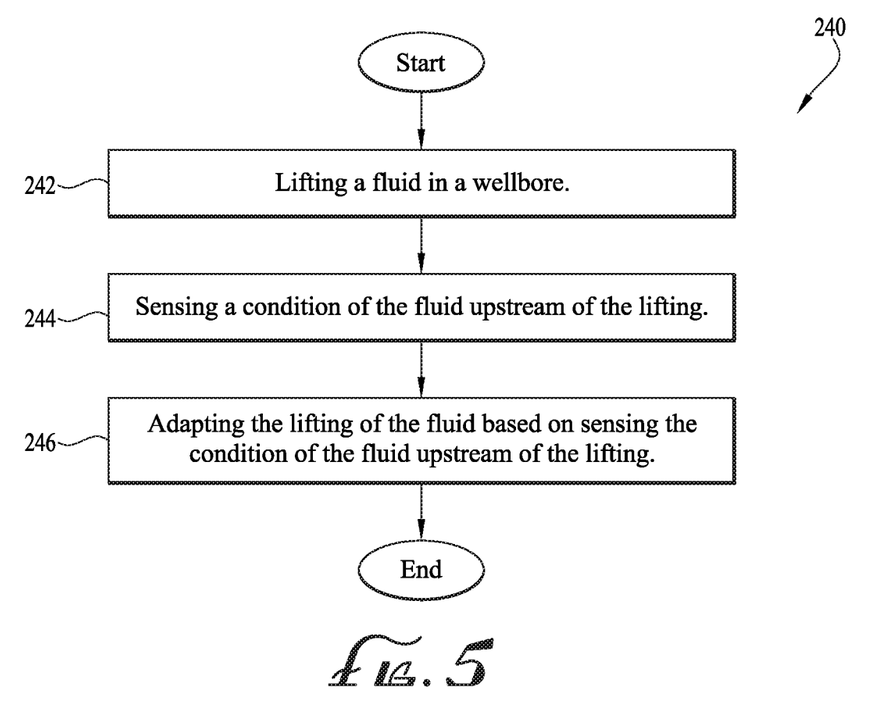
FIG. 5 is a flow chart of yet another method according to an embodiment of the disclosure.

Turning now to FIG. 5, a method 240 is described. In an embodiment, the method 240 comprises a method of producing fluid from a wellbore. At block 242, the method 240 comprises lifting a fluid in a wellbore. At block 244, the method 240 comprises sensing a breaking condition of the fluid upstream of the lifting. Sensing the condition of the fluid upstream of the lifting may comprise sensing one or more parameters of the reservoir fluid 110 flowing in the wellbore 102 at several different locations upstream of the electric motor 112. For example, the parameters may be sensed by sensors associated with the sensor bundles 136 that are located at different positions displaced from each other along the sensor probe 132. At block 246, the method 240 comprises adapting the lifting of the fluid based on sensing the condition of the fluid upstream of the lifting. In an embodiment, the condition is steam breaking into the wellbore upstream of the lifting and adapting the lifting comprises stopping lifting, for example stopping the electric motor 112. In an embodiment, the condition is water breaking into the wellbore upstream of the lifting (e.g., based on an indication of fluid viscosity and/or based on an indication of fluid density) and adapting the lifting comprises reducing a rate of lifting. In an embodiment, the condition is sand breaking into the wellbore upstream of the lifting and adapting the lifting comprises stopping lifting, for example stopping the electric motor 112.

Figure 6:
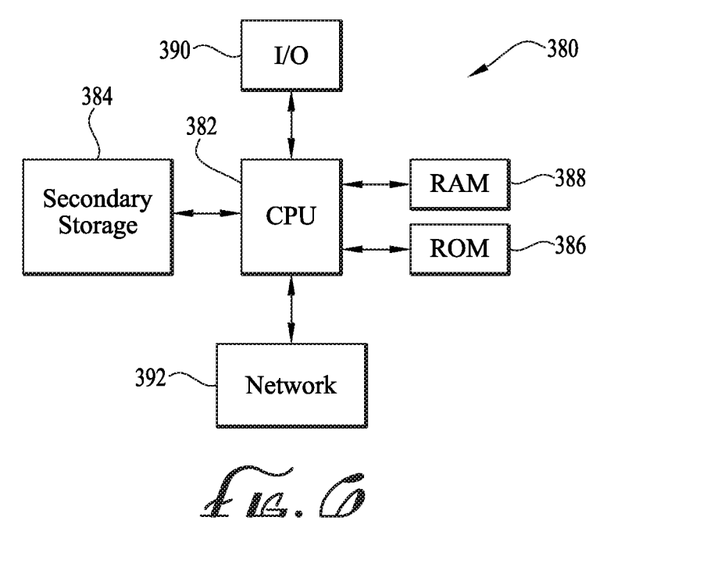
FIG. 6 is a block diagram of a computer system according to an embodiment of the disclosure.

FIG. 6 illustrates a computer system 380 suitable for implementing one or more embodiments disclosed herein. The computer system 380 includes a processor 382 (which may be referred to as a central processor unit or CPU) that is in communication with memory devices including secondary storage 384, read only memory (ROM) 386, random access memory (RAM) 388, input/output (I/O) devices 390, and network connectivity devices 392. The processor 382 may be implemented as one or more CPU chips.

It is understood that by programming and/or loading executable instructions onto the computer system 380, at least one of the CPU 382, the RAM 388, and the ROM 386 are changed, transforming the computer system 380 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

Additionally, after the system 380 is turned on or booted, the CPU 382 may execute a computer program or application. For example, the CPU 382 may execute software or firmware stored in the ROM 386 or stored in the RAM 388. In some cases, on boot and/or when the application is initiated, the CPU 382 may copy the application or portions of the application from the secondary storage 384 to the RAM 388 or to memory space within the CPU 382 itself, and the CPU 382 may then execute instructions that the application is comprised of. In some cases, the CPU 382 may copy the application or portions of the application from memory accessed via the network connectivity devices 392 or via the I/O devices 390 to the RAM 388 or to memory space within the CPU 382, and the CPU 382 may then execute instructions that the application is comprised of. During execution, an application may load instructions into the CPU 382, for example load some of the instructions of the application into a cache of the CPU 382. In some contexts, an application that is executed may be said to configure the CPU 382 to do something, e.g., to configure the CPU 382 to perform the function or functions promoted by the subject application. When the CPU 382 is configured in this way by the application, the CPU 382 becomes a specific purpose computer or a specific purpose machine.

The secondary storage 384 is typically comprised of one or more disk drives or tape drives and is used for non-volatile storage of data and as an over-flow data storage device if RAM 388 is not large enough to hold all working data. Secondary storage 384 may be used to store programs which are loaded into RAM 388 when such programs are selected for execution. The ROM 386 is used to store instructions and perhaps data which are read during program execution. ROM 386 is a non-volatile memory device which typically has a small memory capacity relative to the larger memory capacity of secondary storage 384. The RAM 388 is used to store volatile data and perhaps to store instructions. Access to both ROM 386 and RAM 388 is typically faster than to secondary storage 384. The secondary storage 384, the RAM 388, and/or the ROM 386 may be referred to in some contexts as computer readable storage media and/or non-transitory computer readable media.

I/O devices 390 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 392 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards, and/or other well-known network devices. The network connectivity devices 392 may provide wired communication links and/or wireless communication links (e.g., a first network connectivity device 392 may provide a wired communication link and a second network connectivity device 392 may provide a wireless communication link). Wired communication links may be provided in accordance with Ethernet (IEEE 802.3), Internet protocol (IP), time division multiplex (TDM), data over cable service interface specification (DOCSIS), wave division multiplexing (WDM), and/or the like. In an embodiment, the radio transceiver cards may provide wireless communication links using protocols such as code division multiple access (CDMA), global system for mobile communications (GSM), long-term evolution (LTE), WiFi (IEEE 802.11), Bluetooth, Zigbee, narrowband Internet of things (NB IoT), near field communications (NFC), radio frequency identity (RFID). The radio transceiver cards may promote radio communications using 5G, 5G New Radio, or 5G LTE radio communication protocols. These network connectivity devices 392 may enable the processor 382 to communicate with the Internet or one or more intranets. With such a network connection, it is contemplated that the processor 382 might receive information from the network, or might output information to the network in the course of performing the above-described method steps. Such information, which is often represented as a sequence of instructions to be executed using processor 382, may be received from and outputted to the network, for example, in the form of a computer data signal embodied in a carrier wave.

Such information, which may include data or instructions to be executed using processor 382 for example, may be received from and outputted to the network, for example, in the form of a computer data baseband signal or signal embodied in a carrier wave. The baseband signal or signal embedded in the carrier wave, or other types of signals currently used or hereafter developed, may be generated according to several methods well-known to one skilled in the art. The baseband signal and/or signal embedded in the carrier wave may be referred to in some contexts as a transitory signal.

The processor 382 executes instructions, codes, computer programs, scripts which it accesses from hard disk, floppy disk, optical disk (these various disk based systems may all be considered secondary storage 384), flash drive, ROM 386, RAM 388, or the network connectivity devices 392. While only one processor 382 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 384, for example, hard drives, floppy disks, optical disks, and/or other device, the ROM 386, and/or the RAM 388 may be referred to in some contexts as non-transitory instructions and/or non-transitory information.

In an embodiment, the computer system 380 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an embodiment, virtualization software may be employed by the computer system 380 to provide the functionality of a number of servers that is not directly bound to the number of computers in the computer system 380. For example, virtualization software may provide twenty virtual servers on four physical computers. In an embodiment, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an embodiment, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 380, at least portions of the contents of the computer program product to the secondary storage 384, to the ROM 386, to the RAM 388, and/or to other non-volatile memory and volatile memory of the computer system 380. The processor 382 may process the executable instructions and/or data structures in part by directly accessing the computer program product, for example by reading from a CD-ROM disk inserted into a disk drive peripheral of the computer system 380. Alternatively, the processor 382 may process the executable instructions and/or data structures by remotely accessing the computer program product, for example by downloading the executable instructions and/or data structures from a remote server through the network connectivity devices 392. The computer program product may comprise instructions that promote the loading and/or copying of data, data structures, files, and/or executable instructions to the secondary storage 384, to the ROM 386, to the RAM 388, and/or to other non-volatile memory and volatile memory of the computer system 380.

In some contexts, the secondary storage 384, the ROM 386, and the RAM 388 may be referred to as a non-transitory computer readable medium or a computer readable storage media. A dynamic RAM embodiment of the RAM 388, likewise, may be referred to as a non-transitory computer readable medium in that while the dynamic RAM receives electrical power and is operated in accordance with its design, for example during a period of time during which the computer system 380 is turned on and operational, the dynamic RAM stores information that is written to it. Similarly, the processor 382 may comprise an internal RAM, an internal ROM, a cache memory, and/or other internal non-transitory storage blocks, sections, or components that may be referred to in some contexts as non-transitory computer readable media or computer readable storage media.

ADDITIONAL DISCLOSURE

The following are non-limiting, specific embodiments in accordance with the present disclosure:

A first embodiment, which is an electric submersible pump (ESP) assembly, comprising an electric motor, a centrifugal pump mechanically coupled to the electric motor, and a probe mechanically coupled to the electric motor and extending upstream of the electric motor, comprising a plurality of sensor bundles distributed axially along the probe wherein each sensor bundle comprises at least one sensor.

A second embodiment, which is the ESP assembly of the first embodiment, wherein the probe comprises at least one centralizer.

A third embodiment, which is the ESP assembly of the first or the second embodiment, wherein the probe comprises a plurality of centralizers, wherein each sensor bundle is associated with at least one centralizer located proximate to the sensor bundle.

A fourth embodiment, which is the ESP assembly of the third embodiment, wherein each sensor bundle is associated with a centralizer located upstream and proximate to the sensor bundle and with a centralizer located downstream and proximate to the sensor bundle.

A fifth embodiment, which is the ESP assembly of the first, the second, the third, or the fourth embodiment, wherein the probe is at least about 10 feet long and less than about 1000 feet long.

A sixth embodiment, which is the ESP assembly of the first, the second, the third, the fourth, or the fifth embodiment, wherein the probe is less than about 300 feet long.

A seventh embodiment, which is the ESP assembly of the first, the second, the third, the fourth, the fifth, or the sixth embodiment, wherein the at least one sensor is selected from the group consisting of a temperature sensor, a pressure sensor, a density sensor, a viscosity sensor, an acoustic sensor, a vibration sensor, and an acceleration sensor.

An eighth embodiment, which is the ESP assembly of the first, the second, the third, the fourth, the fifth, the sixth, or the seventh embodiment, wherein the sensor bundles are removably coupled to the probe.

A ninth embodiment, which is the ESP assembly of the first, the second, the third, the fourth, the fifth, the sixth, the seventh, or the eighth embodiment, wherein the sensor bundles comprise communication components that promote communicating sensor data using wired communication, wireless communication, acoustic communication, or hydraulic communication.

A tenth embodiment, which is the ESP assembly of the first, the second, the third, the fourth, the fifth, the sixth, the seventh, the eighth, or the ninth embodiment, comprising at least one communication hub that is configured to receive sensor data from a plurality of sensors and to send sensor data.

An eleventh embodiment, which is a method of artificially lifting fluid in a wellbore, comprising sending a first control signal from a controller located at a surface location proximate to a wellbore to an electric drive located at the surface location, sending a first electric power signal by the electric drive to an electric submersible pump (ESP) assembly located in the wellbore, where the first electric power signal is generated by the electric drive based on the first control signal, providing mechanical torque by an electric motor of the ESP assembly to a centrifugal pump of the ESP assembly based on the first electric power signal, determining a first fluid flow parameter value by a first sensor mechanically coupled to a probe of the ESP assembly located upstream of the electric motor, determining a second fluid flow parameter value by a second sensor mechanically coupled to the probe of the ESP assembly, where the second sensor is located upstream of the first sensor, sending the fluid flow parameter values by the sensors to the controller, generating a second control signal by the controller based on the fluid flow parameter values, sending the second control signal by the controller to the electric drive, sending a second electric power signal to the ESP assembly by the electric drive, where the second electric power signal is generated by the electric drive based on the second control signal, and providing mechanical torque by the electric motor to the centrifugal pump based on the second electric power signal.

A twelfth embodiment, which is the method of the eleventh embodiment, wherein the first control signal is generated by the controller based on fluid flow parameter values received by the controller at a first time from the first and second sensors, the second control signal is generated by the controller based on fluid flow parameter values received by the controller at a second time from the first and second sensors, where the second time is later than the first time.

A thirteenth embodiment, which is the method of the eleventh or the twelfth embodiment, wherein the fluid flow parameter values are a fluid flow temperature, a fluid flow pressure, a fluid flow density, or a fluid flow viscosity.

A fourteenth embodiment, which is the method of the eleventh, the twelfth, or the thirteenth embodiment, wherein the second control signal is generated by the controller based on a plurality of different fluid flow parameters.

A fifteenth embodiment, which is the method of the eleventh, the twelfth, the thirteenth, or the fourteenth embodiment, wherein the first electric power signal differs from the second electric power signal in frequency.

A sixteenth embodiment, which is the method of the eleventh, the twelfth, the thirteenth, the fourteenth, or the fifteenth embodiment, wherein the first electric power signal differs from the second electric power signal in voltage.

A seventeenth embodiment, which is a method of artificially lifting fluid in a wellbore, comprising mechanically coupling a top of a probe to a bottom of an artificial lift assembly, wherein the probe comprises a plurality of sensors, running the probe and the artificial lift assembly into a wellbore, operating the artificial lift assembly to lift fluid to a wellhead of the wellbore, where operation of the artificial lift assembly is controlled by a controller located at the surface proximate to the wellhead, determining fluid flow parameter values of the fluid flowing in the wellbore upstream of the artificial lift assembly, and transmitting fluid flow parameter values by the sensors to the controller, wherein the controller controls the operation of the artificial lift assembly at least in part based on the fluid flow parameter values.

An eighteenth embodiment, which is the method of the seventeenth embodiment, further comprising mechanically coupling a plurality of sensor bundles to the probe, wherein each sensor bundle comprises a plurality of sensors.

A nineteenth embodiment, which is the method of the seventeenth or the eighteenth embodiment, wherein the artificial lift assembly is an electric submersible pump (ESP) assembly, a rod lift assembly, a plunger lift assembly, a gas lift assembly, or a charge pump assembly.

A twentieth embodiment, which is the method of the seventeenth, the eighteenth, or the nineteenth embodiment, wherein the fluid flow parameter values comprise fluid pressure and fluid temperature, fluid pressure and fluid viscosity, fluid pressure and fluid density, fluid temperature and fluid viscosity, fluid temperature and fluid density, or fluid density and fluid viscosity.

A twenty-first embodiment, which is a method of producing fluid from a wellbore, comprising lifting a fluid in a wellbore, sensing a breaking condition of the fluid upstream of the lifting, and adapting the lifting of the fluid based on sensing the condition of the fluid upstream of the lifting.

A twenty-second embodiment, which is the method of the twenty-first embodiment, wherein the condition is steam breaking into the wellbore upstream of the lifting and adapting the lifting comprises stopping the lifting.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An electric submersible pump (ESP) assembly, comprising:
    an electric motor;
    a centrifugal pump mechanically coupled to the electric motor; and
    a probe structure mechanically coupled to the electric motor and extending upstream of the electric motor; and
    a plurality of sensor bundles coupled to the probe structure and distributed axially along the probe structure, wherein each sensor bundle comprises at least one sensor.

2. The ESP assembly of claim 1, wherein the probe comprises at least one centralizer.

3. The ESP assembly of claim 1, wherein the probe comprises a plurality of centralizers, wherein each sensor bundle is associated with at least one centralizer located proximate to the sensor bundle.

4. The ESP assembly of claim 3, wherein each sensor bundle is associated with a centralizer located upstream and proximate to the sensor bundle and with a centralizer located downstream and proximate to the sensor bundle.

5. The ESP assembly of claim 1, wherein the probe is at least about 10 feet long and less than about 1000 feet long.

6. The ESP assembly of claim 1, wherein the probe is less than about 300 feet long.

7. The ESP assembly of claim 1, wherein the at least one sensor is selected from the group consisting of a temperature sensor, a pressure sensor, a density sensor, a viscosity sensor, an acoustic sensor, a vibration sensor, or an acceleration sensor.

8. The ESP assembly of claim 1, wherein the sensor bundles are removably coupled to the probe.

9. The ESP assembly of claim 1, wherein the sensor bundles comprise communication components that promote communicating sensor data using communication selected from the group consisting of wired communication, wireless communication, acoustic communication, and hydraulic communication.

10. The ESP assembly of claim 1, comprising at least one communication hub that is configured to receive sensor data from a plurality of sensors and to send sensor data.

11. A method of artificially lifting fluid in a wellbore, comprising:
    sending a first control signal from a controller located at a surface location proximate to the wellbore to an electric drive located at the surface location;
    sending a first electric power signal by the electric drive to an electric submersible pump (ESP) assembly located in the wellbore, where the first electric power signal is generated by the electric drive based on the first control signal;
    providing mechanical torque by an electric motor of the ESP assembly to a centrifugal pump of the ESP assembly based on the first electric power signal;
    determining a first fluid flow parameter value by a first sensor mechanically coupled to a probe of the ESP assembly located upstream of the electric motor;
    determining a second fluid flow parameter value by a second sensor mechanically coupled to the probe of the ESP assembly, where the second sensor is located upstream of the first sensor;
    sending the first and second fluid flow parameter values by the sensors to the controller;
    generating a second control signal by the controller based on the first and second fluid flow parameter values;
    sending the second control signal by the controller to the electric drive;
    sending a second electric power signal to the ESP assembly by the electric drive, where the second electric power signal is generated by the electric drive based on the second control signal; and
    providing mechanical torque by the electric motor to the centrifugal pump based on the second electric power signal.

12. The method of claim 11, wherein the first control signal is generated by the controller based on first and second fluid flow parameter values received by the controller at a first time from the first and second sensors, the second control signal is generated by the controller based on first and second fluid flow parameter values received by the controller at a second time from the first and second sensors, where the second time is later than the first time.

13. The method of claim 11, wherein the first and second fluid flow parameter values are a fluid flow temperature, a fluid flow pressure, a fluid flow density, or a fluid flow viscosity.

14. The method of claim 11, wherein the first sensor is a first kind of sensor and the second sensor is a second kind of sensor, where the second kind of sensor is different from the first kind of sensor.

15. The method of claim 11, wherein the first electric power signal differs from the second electric power signal in frequency.

16. The method of claim 11, wherein the first electric power signal differs from the second electric power signal in voltage.

17. A method of artificially lifting fluid in a wellbore, comprising:
    mechanically coupling a top of a probe structure to a bottom of an artificial lift assembly, wherein a plurality of sensors are coupled to the probe structure and distributed axially along the probe structure;
    running the probe structure and the artificial lift assembly into the wellbore;
    operating the artificial lift assembly to lift fluid to a wellhead of the wellbore, where operation of the artificial lift assembly is controlled by a controller located at the surface proximate to the wellhead;
    determining fluid flow parameter values of the fluid flowing in the wellbore upstream of the artificial lift assembly; and
    transmitting fluid flow parameter values by the sensors to the controller, wherein the controller controls the operation of the artificial lift assembly at least in part based on the fluid flow parameter values.

18. The method of claim 17, further comprising mechanically coupling a plurality of sensor bundles to the probe, wherein each sensor bundle comprises a plurality of sensors.

19. The method of claim 17, wherein the artificial lift assembly is an electric submersible pump (ESP) assembly, a rod lift assembly, a plunger lift assembly, a gas lift assembly, or a charge pump assembly.

20. The method of claim 17, wherein the fluid flow parameter values comprise fluid pressure and fluid temperature, fluid pressure and fluid viscosity, fluid pressure and fluid density, fluid temperature and fluid viscosity, fluid temperature and fluid density, or fluid density and fluid viscosity.

\* \* \* \* \*